(12) United States Patent
Kindiger

(10) Patent No.: US 8,912,388 B2
(45) Date of Patent: Dec. 16, 2014

(54) LOLIUM MULTIFLORUM LINE INDUCING GENOME LOSS

(71) Applicant: The United States of America as represented by the Secretary of Agriculture, Washington, DC (US)

(72) Inventor: Bryan K. Kindiger, El Reno, OK (US)

(73) Assignee: The United States of America, as represented by the Secretary of Agriculture, Washington, DC (US)

(*) Notice: Subject to any disclaimer, the term of this patent is extended or adjusted under 35 U.S.C. 154(b) by 0 days.

(21) Appl. No.: 13/692,080

(22) Filed: Dec. 3, 2012

(65) Prior Publication Data
US 2013/0097736 A1 Apr. 18, 2013

Related U.S. Application Data

(62) Division of application No. 12/565,350, filed on Sep. 23, 2009, now abandoned.

(60) Provisional application No. 61/101,218, filed on Sep. 30, 2008.

(51) Int. Cl.
| | |
|---|---|
| *A01H 1/02* | (2006.01) |
| *A01H 1/08* | (2006.01) |
| *A01H 5/00* | (2006.01) |
| *A01H 5/10* | (2006.01) |
| *A01H 4/00* | (2006.01) |

(52) U.S. Cl.
CPC .. *A01H 1/02* (2013.01); *A01H 5/10* (2013.01); *A01H 5/00* (2013.01)
USPC ........... 800/269; 800/299; 800/303; 800/320; 435/410

(58) Field of Classification Search
None
See application file for complete search history.

(56) References Cited

U.S. PATENT DOCUMENTS

2004/0199936 A1* 10/2004 Gaue et al. .................... 800/274

OTHER PUBLICATIONS

Werner, M. Genetica Polonica 24(2): 139-148 (1983).*
Zwierzykowski, Z. Genetica Polonica 21(3): 259-272 (1980).*
Potrykus et al. Molecular and General Genetics 199: 183-188 (1985).*
Zwierzykowski et al. Plant Breeding 117: 457-462 (1998).*

* cited by examiner

*Primary Examiner* — David T Fox
(74) *Attorney, Agent, or Firm* — David L. Marks; John D. Fado; Lesley Shaw

(57) ABSTRACT

Dihaploid homozygous Fescue species may be produced by interspecific hybridization of Fescue with novel ryegrass, *Lolium multiflorum*, lines, that induce genome loss. Plants that are dihaploid homozygous *Lolium* and amphidiploids are also produced.

20 Claims, 2 Drawing Sheets

FIGURE 1

Inducer (Ryegrass = 14 chromosomes (7R 7R) X Tall Fescue (42 chromosomes, 3 pairs of 7; 7a1 7a1, 7a2 7a2, 7b 7b)

True Ryegrass-Tall Fescue F1's
7R + 7a1 7a2 7b (28 chromosomes total; 7R + 21 TF = 28)

Plant the F1 generated interspecific hybrid seed and allow the plants to grow.

Allow the F1 plants to flower and seed heads to mature. Because the F1 plants are sterile, NO pollen is required or available.

Sow the seed heads into soil, F2 plants will arise.
Since no pollen, F2 plants (embryos) arise via parthenogenesis)

F2 Generation: Types of Plants Recovered from the F1 are :
1. Recovered Dihaploid Ryegrass with 14 chromosomes
2. Recovered Dihaploid Tall Fescue with 42 chromosomes
3. Recovered Amphidiploids (possess 14 ryegrass + 42 Tall fescue chromosomes)
4. Recovered 28 chromosomes (the original F1 plants, 7R + 21 TF chromosomes)
5. Recovered 35 chromosomes individuals (possess balanced doses of the ryegrass and TF genomes)
6. Aneuploids (individuals with an infinite combinations of unbalanced chromosome numbers)

FIGURE 2

Inducer (Ryegrass = 14 chromosomes (7R 7R) X Tall Fescue (42 chromosomes, 3 pairs of 7; 7a1 7a1, 7a2 7a2, 7b 7b)

The True Ryegrass-Tall Fescue F1's
7R + 7a1 7a2 7b (28 chromosomes total; 7R + 21 TF = 28)

Sow the F1 generated interspecific hybrid seed and allow the plants to grow to F1 plants, mature and flower.

During their growth cycle, many of the F1 hybrids will form chimeral sectors that LOOSE all the ryegrass genome (7R), leaving only the tall fescue chromosomes (7a1, 7a2, 7b). These pure tall fescue growing shoots (apical meristems) will spontaneously double, resulting in a recovered tall fescue (7a1 7a1, 7a2 7a2, 7b 7b) that is also fertile and is considered a dihaploid, with fixation across all loci; it can also be called an inbred line).

This loss of the ryegrass genome is due to somatic loss, or ryegrass genome instability in the hybrid situation. This behavior occurs in the 28 chromosome recovered F2's (Figure 1).

In 28 chromosome F1's and F2's exhibiting these sectors the wider leafed region are the fescue sector which will produce the dihaploid fescue.

LOLIUM MULTIFLORUM LINE INDUCING GENOME LOSS

CROSS-REFERENCE TO RELATED APPLICATIONS

This application is a divisional application of U.S. application Ser. No. 12/1565350 filed on Sep. 23, 2009 which is abandoned, and which claims the benefit under 35 U.S.C. 1.19(e) of U.S. provisional 61/101,218, filed Sep. 30. 2008, the contents of which are incorporated by reference herein.

BACKGROUND OF THE INVENTION

1. Field of the Invention

This invention relates to a novel diploid *Lolium multiflorum* line and a method of using the same to produce dihapioid homozygous *Lolium* and *Festuca* species.

2. Description of the Prior Art

Turf and forage grass cultivars are essentially germplasm synthetics segregating for a multitude of genes. Most if not all forage grass cultivars are developed from traditional mass, phenotypic recurrent or half-sib selection methods. However, the availability of homozygous lines, also called inbred lines, can provide completely new approaches for breeding and grass cultivar development. In one application, such dihapioid lines could be utilized for F1 hybrid development, taking advantage of the power of heterosis to increase biomass production, increase stress resistance, increase insect and disease resistance, etc.

However, the successful, reproducible development of such hybrids would require the availability of true breeding, homozygous dihaploid parental lines. Currently, the only techniques for generating homozygous dihaploid Fescue is through the use of anther-microspore culture, followed by genome doubling techniques. These techniques are time consuming, labor intensive, and unpredictable due to the unknown genetic predisposition that a segregating germplasm may exhibit toward such culture and genome doubling techniques. Essentially, this is an unpredictable approach for the generation of homozygous lines since only trial and error, and experience can be used to determine which particular cultivars are amendable to such a technique.

SUMMARY OF THE INVENTION

Novel ryegrass, *Lolium multiflorum*, lines, referred to herein as inducer lines, have been discovered which may be crossed with species representing the genus of Fescue, *Festuca*, with the interspecific hybrid subsequently incurring genome loss to produce Fescue and *Lolium* (ryegrass) dihapioid individuals that are homozygous for all loci across each species respective genomes. In addition, dihapioid amphidipioid *Lolium*-Fescue lines also are a result of the original hybridizations. These *L. multiflorum* inducer lines are either fully pollen fertile, partially sterile (leaky) or completely pollen sterile, and are characterised by the property that upon interspecific hybridization as the maternal parent using a *Festuca* species as the male parent, confer to the resultant sterile F1 interspecific hybrids, the ability to lose either the *Lolium* or *Festuca* genome via somatic loss during megaspore (egg) development; followed by a low level of a parthenogenic seed development response, that results in the production of some seed in the panicle which exhibits a viable embryo and the lack of a normally developed endosperm. When sown, seedlings originating from these parthenogenic seed produce an F2 generation where at least some of which are dihapioid homozygous *Festuca* lines comprising a karyotype exhibitlog a balanced genome of *Festuca* chromosomes, equivalent to the chromosome number of their *Festuca* parent, with a complete absence of all *Lolium* chromosomes. Other F2 plants are produced as well, including dihapioid homozygous *Lolium* having a complete loss of the *Festuca* genome; and homozygous amphidipioids which have no loss in either the *Lolium* or Fescue genome.

Dihapioid homozygous *Festuca* species may also be generated directly from these same F1 interspecific hybrids without the need for parthenogenic seed development and the subsequent F2 generation. During the growth cycle of the F1 interspecific hybrids, many of the F1 plants eventually form somatic sectors that result from the complete loss of all their ryegrass genome and appear phenotypically as Fescue growing shoots. Sectors having only this haploid Fescue chromosome constitution spontaneously double, resulting in a dihapioid fescue sector possessing a full complement of the parental fescue genome. These Fescue somatic sectors can be retained, and will develop into mature, dihapioid homozygous *Festuca* plants possessing a balanced genome of *Festuca* chromosomes equivalent to the chromosome number of the *Festuca* paternal parent with a complete absence of *Lolium* chromosomes.

Mature dihapioid homozygous *Festuca* plants produced from the interspecific hybridization using either of the above-mentioned techniques are fertile, and may be utilised in crosses with other dihapioid *Festuca* recoveries to produce true F1 hybrid *Festuca* or can be combined in a series of hybridizations to develop polycross hybrid populations.

In accordance with this discovery, it is an object of this invention to provide a novel ryegrass, *Lolium multiflorum*, line that may be used to produce dihapioid homozygous *Festuca* species.

Another object of this invention to provide novel ryegrass, *Lolium multiflorum*, lines that may be used to produce not only dihapioid homozygous *Festuca* species but also dihapioid homozygous *Lolium* species and/or homozygous *Lolium-Fescue* amphidipioids.

A further object of this invention is to provide a method for producing dihapioid homozygous *Festuca* lines which are effective as inbred lines and may be crossed with any other dihapioid Fescue recovery to produce true F1 hybrid *Fescue*.

Yet another object of this invention to provide a simple, reproducible, and relatively fast method for producing dihapioid homozygous *Festuca* species.

Other objects and advantages of this invention will become readily apparent from the ensuing description.

BRIEF DESCRIPTION OF THE DRAWINGS

FIG. 1 shows a diagram of dihapioid generation via parthogenesis in accordance with a first embodiment of the invention.

FIG. 2 shows a diagram of dihapioid generation via chimeral sectors in the F1 or F2 generations, in accordance with a second embodiment of the invention.

DETAILED DESCRIPTION OF THE INVENTION

A sample of at least 2,500 seeds of each of the preferred novel ryegrass, *Lolium multiflorum*, lines of this invention, referred to herein as inducer line IL-1 and inducer line IL-2, and which may be used to produce dihapioid homozygous *Festuca* species, have been deposited under the conditions of the Budapest Treaty with the American Type Culture Collection (10801 University Blvd, Manassas, Va., 20110-2209, USA) on Jul. 22, 2009, and Aug. 28, 2009, respectively, and have been assigned deposit accession nos. ATCC PTA-10229 and ATCC PTA-10315, respectively.

The inducer lines of this invention are *Lolium multiflorum* (Italian ryegrass or annual ryegrass) a diploid (2n=2x=14), herbaceous annual grass, exhibiting phenotypic traits typical of this species as described by Wheeler (Forage and Pasture Crops, A Handbook of Information about the Grasses and Legumes Grown for Forage in the United States. Van Nostrand Company. New York. 1950. pp. 537-541) and Quattrocchi (CRC World Dictionary of Grasses: Common Names, Scientific Names, Eponyms, Synonyms, and Etymology. CRC Press. Boca Raton, Fla., USA, 2006. p. 2408), the contents of which are incorporated by reference herein. The inducer line IL-1 is a leaky pollen sterile line that is uniquely characterized toy its ability, upon interspecific hybridization as a maternal parent with a *Festuca* species being used as the paternal parent to 1) confer to the resultant sterile F1 interspecific hybrids the ability to generate a low level of a parfchenogenic response and produce some seed in the panicle (i.e., seed heads) that possess a viable embryo; and 2) induce genome loss following the interspecific hybridization as described herein.

Induction of genome loss following interspecific hybridization generates dihaploid homozygous *Festuca* species comprising a karyotype (nuclear genome) of *Festuca* chromosomes equal to the chromosome number of the *Festuca* male parent (i.e., they retain a full complement of *Festuca* chromosomes with their chromosome number being the same as the *Festuca* male parent) with no *Lolium* chromosomes. Possessing a full complement of *Festuca* chromosomes and no *Lolium* chromosomes, these dihaploid homozygous *Festuca* species appear as normal Fescue plants. For example, in a preferred embodiment using Tall Fescue, *Festuca arundinaceae* (also referred to as *Lolium arundinaceae*), as the male parent, the resultant dihapioid homozygous *Festuca* comprise a karyotype of 42 *Festuca* chromosomes. Alternatively, using Meadow Fescue, *F. pratensis*, as the male parent, the resultant dihapioid homozygous *Festuca* would comprise a karyotype of 14 *Festuca* chromosomes. As described in detail herein below, depending upon the particular technique used, other dihaploid homozygous plants, including dihaploid homozygous *Lolium multiflorum*, as well as dihaploid homozygous amphidiploids may also be recovered. The dihaploid homozygous *Lolium multiflorum* plants comprise a karyotype of 14 *Lolium multiflorum* chromosomes and appear as normal ryegrass plants, while the generation of amphidiploids do not undergo genome loss, but result only from spontaneous genome doubling, and comprise a karyotype of 14 *Lolium multiflorum* chromosomes (representative of the maternal parent) and *Festuca* chromosomes equal to the chromosome number of the *Festuca* male parent (e.g., 42 *Festuca* chromosomes when using Tall Fescue). Significantly, these dihaploid homozygous *Lolium multiflorum* may be used as new inducer lines for interspecific hybridization with Fescue as described herein. Although any of these dihaploid homozygous *Lolium* may be recovered and used as inducers as described herein, it is preferable to utilize those recoveries that appear healthy and vigorous. Moreover, these dihaploid homozygous *Lolium* may be used directly as inducers in crosses without requiring a generation of seed production or offspring from such seed.

For the purpose of this invention, any fully pollen fertile, completely pollen sterile or partially pollen sterile *Lolium multiflorum*, having the identifying characteristics of line IL-1, including progeny or variants thereof which retain the ability, upon interspecific hybridization as a maternal parent with a *Festuca* species as the paternal parent, to 1) confer to the resultant sterile F1 interspecific hybrids the ability to generate a low level of a parthenogenic response and produce some seed in the panicle that possess a viable embryo; and 2) induce genome loss following the interspecific hybridization, are effective as inducers. The term variant is defined herein to include transformants and mutants of line IL-1. For example, in accordance with this invention, the IL-1line may be modified to include heterologous genes and/or mutations in the genes therein. Transformation techniques which may be used herein include but are not limited to microparticle gene transfer such as described by Lowe et al. (1995, Bio/Technology, 13:677-682), pollen transformation techniques such as described by Ohta (1986, Proc. Nat'l Acad. Sci. USA, 83:715-719), Smith et al. (1994, Plant Science, 104:49-58), and deWet (International Patent Application WO 85/01856), electroporation techniques such as described by Rhodes (1988, Science, 240:204-207), Krzyzk et al. (U.S. Pat. No. 5,384,253), and viral transformation such as described by Langenberg et al. (U.S. Pat. No. 5,416,010). Techniques for introducing mutations include but are not limited to conventional chemical or irradiation techniques for random mutagenesis, or insertional or site directed point mutagenesis processes such as described by Neuffer ["Induction of Genetic Variability", In: Maize Breeding and Genetics, Walden (ed.), 1978, pp. 579-600]. The contents of each of the above-mentioned references are incorporated by reference herein.

As noted above, additional inducer lines may be developed from the inducer line IL-1. Two of these new lines, referred to herein as IL-2 and IL-3, were each derived from, single plant selections from the original IL-1 population. Because IL-1 is a "leaky" pollen sterile population that segregates a range of sterility levels, additional, inducer lines can be generated from IL-1 through typical plant selection procedures. One such method involves examination of individual plants within the IL-1 population, with inducer lines IL-2 and IL-3 being selected from IL1 on the basis of their higher level of pollen sterility and improved vigor, both in comparison to the overall or mean of the IL-1 population. Thus, both IL-2 and IL-3 have a narrower genetic base (defined herein as reduced or limited genetic variation) than their IL-1 parent). However, since Il2 and IL3 represent two different, individual plant selections, they will possess differing genotypes from IL1 and each other. Both IL-2 and IL-3 exhibit a significantly increased level of pollen sterility, increased plant height, and shorter time to flower, than IL-1. Of these, IL-2 is particularly preferred as it exhibits the greatest increase in the level of pollen sterility and plant height, and the shortest time to flower. Each of IL-2 and IL-3 are *Lolium multiflorum* (Italian ryegrass or annual ryegrass) a diploid (2n=2x=14), herbaceous annual grass, exhibiting phenotypic traits typical of this species as described by Wheeler (Ibid) and Quattrocohi (ibid). Each of IL-2 and IL-3 are also effective inducer lines, and as such are characterized by their ability, upon interspecific hybridization as a maternal parent with a *Festuca* species being used as the paternal parent to 1) confer to the resultant sterile F1 interspecific hybrids the ability to generate a low level of a partheoogenic response and produce some seed in the panicle (i.e., seed heads) that possess a viable embryo; and 2) induce genome loss following the interspecific hybridization as described herein. In addition, both IL2 and IL3 also provide for the allowance of somatic sectors in the generated F1 hybrids which can result in the further generation of DH *Lolium* lines.

Another aspect of this invention is to provide for ceils which upon growth and differentiation produce *Lolium mul-*

*tiflorum* plants which are effective as inducer lines, such that upon interspecific hybridization as a maternal parent with a *Festuca* species as the paternal parent, they 1) confer to the resultant sterile F1 interspecific hybrids the ability to generate a low level of a parthenogenic response and produce some seed in the panicle that possess a viable embryo; and 2) induce genome loss following the interspecific hybridization. Thus, as used herein, she term "*L. multiflorum* plant or parts thereof" includes plant cells, plant protoplasts, plant cells of tissue culture from which *L. multiflorum* plants can be regenerated, plant calli, plant clumps, as well as plant cells that are intact in plants or parts of plants such as, seed, flowers, embryos, ovules, roots, root tips, pollen, leaves, stalks, and the like.

The *L. multiflorum* inducer lines of this invention are stably maintained by conventional intercrossing or selfing.

In a first preferred embodiment shown in FIG. 1, the *L. multiflorum* inducer line is crossed as a maternal parent with any desired *Festuca* species being utilized as the paternal parent, and the resultant F1 interspecific hybrid seed is sown and allowed to grow into F1 plants, thereby they can mature and flower. The F1 plants comprise a karyotype of 7 *Lolium multiflorum* chromosomes plus a contributed haploid chromosome set from the paternal *Festuca* parent (e.g. 21 *Festuca* chromosomes whan using *Festuca* arundinaceae, 7 chromosomes when using *Festuca pratensis*, etc.) As is typical for most wide cross or interspecific hybrids with unbalanced genomes or differing chromosome number contributions, the F1 plants are typically both pollen and seed sterile. However, despite this sterility, a low level of parthenogenesis produces some seed in the panicle that possess a viable embryo; and lacks an obvious endosperm. The seed heads from the F1 plants are collected, preferably rubbed to remove seed husks surrounding the parthenogenic seed, then sown and allowed to grow, such that any of those of seeds that have developed embryos via parthenogenesis will develop into F2 plants. The F2 plants that are recovered are primarily (nearly 50% each) diploid homozygous Fescue with no *Lolium* chromosomes (comprising a karyotype of a balanced genome of *Festuca* chromosomes equal to the chromosome number of the *Festuca* paternal parent, 42 when using Tall Fescue) and diploid homozygous ryegrass with no *Festuca* chromosomes (comprising a karyotype of 14 *Lolium multiflorum* chromosomes representative of the maternal parent). A low frequency of mixed genotypes are also produced, most notably amphidiplcids which comprise a karyotype of 14 *Lolium multiflorum* chromosomes (representative of the maternal parent) plus *Festuca* chromosomes equal to the chromosome number of the *Festuca* paternal parent (42when, using Tall Fescue, providing a total chromosome number of 56).

The recovered F1 or F2 dihaploid homozygous *Festuca*'s and *Lolium*'sare not genetically identical to their parents since each interspecific hybrid represents a randomly generated haplold gamete/egg provided from each parent. In fact, each dihaploid *Lolium* or *Festuca* recovery represents only a single possible gens combination out of billions of possibilities. Essentially, the generation of the interspecific hybrids is a form of gamete selection through the pollen (in the case of the *Festuca* parent) or through the egg (in the case of the *Lolium* parent). The dihaploid *Lolium* and *Festuca* and amphidipioid recoveries are both male and female fertile and maintain their dihaploid genotypes by selfing or sibbing; they remain fixed at ail loci (dihaploid), and are suitable for potential use as inbred lines for mapping studies, population development, selection, and breeding. Moreover, since the dihaploids are generated utilizing the *Lolium* as the maternal parent in the interspecific cross, all of the progeny, including the F2 dihaploid homozygous *Festuca* and homozygous amphidipioids, will retain the extranuclear genes and cytoplasm (including mitochondrial or cytoplasm and chloroplasts) of the *Lolium multiflorum* inducer parent. The presence of *Lolium* extranuclear genes in the dihaploid homozygous *Festuca* allows these plants to be readily distinguished from any dihaploid homozygous *Festuca* which might be produced using conventional techniques, such as use of anther-microspore culture followed by chromosome doubling. Extranuciear *Lolium* genes may be detected, for example, by conventional mitochondrial DNA or cytoplasmic analysis techniques [McGrath, Hodkinson, Salamin and Barth, 2006; Development and testing of novel chloroplast microsateilite markers for *Lolium perenne* and other grasses (Poaceae) from de novo sequencing and in silica sequences. Molecular Ecology Notes 6:449-452]

In an alternative preferred embodiment shown in FIG. 2, the dihaploid homozygous *Festuca* species may be produced directly from the same F1 interspecific hybrids described above, without the need for generating an F2 generation. In this embodiment, the *L. multiflorum* inducer line is crossed as the maternal parent with a *Festuca* species as the paternal parent to generate sterile F1 interspecific hybrid plants in the same manner as described above. Again, these F1 hybrids initially comprise a karyotype of 7 *Lolium multiflorum* chromosomes plus 21 *Festuca* chromosomes if, as example, an *F. arundinaceae* is utilised as the paternal parent. During the growth stage of the F1 interspecific hybrids, many of the F1 hybrids eventually form somatic (chimeral) sectors that have lost all of their ryegrass genome (7R) and retain only the Fescue chromosomes. The occurrence of this event is random and can occur early on; such as the seedling stage or very late in the plants growth phase such as the flowering stage. These chimera1 sectors appear as Fescue growing shoots (i.e., apical meristems) from the F1 plant. Loss of the ryegrass genome is due to somatic loss or ryegrass genome instability in the interspecific hybrid condition. These Fescue somatic sectors will have their *Festuca* genome double spontaneously, without induction, generating a dihaploid homoKygous *Festuca* sector (tiller) possessing a full balanced complement of *Festuca* chromosomes and no *Lolium* chromosomes. The Fescue somatic sectors can be readily identified and distinguished from ryegrass sectors and the ryegrass-Fescue hybrid by their appearance as normal. *Fescue*, that is, exhibiting often wider leaves, rough leaf texture, alteration in leaf color and at flowering maturity, and a typical Fescue inflorescence/panicle.

These Fescue somatic sector regions may be removed and transferred to another pot, and will develop into mature, fertile dihaploid homozygous *Festuca* individuals, fixed for all loci, and comprising a karyotype of a balanced genome of *Festuca* chromosomes equal to the chromosome number of the *Festuca* paternal parent (42 when using Tall Fescue) with no *Lolium* chromosomes. The Fescue somatic sectors may be removed from the interspecific hydrid and transferred to pots or field nursery. The fescue sectors are perennial and can be maintained indefinitely by vegetative propagation or via seed. As in the previous embodiment, the resultant F2 dihaploid homozygous *Festuca* plants will retain the extranuclear genes (mitochondrial DNA and cytoplasm) of *Lolium multiflorum*. Although the process has been described as identifying and retaining Fescue somatic sectors from the F1generation of plants, it is understood that Fescue somatic sectors can also develop in any subsequent generation of hybrid plants that may possess a haploid set of chromosomes from the *Lolium* or *Festuca* parents (e.g., 28 chromosomes in the case of *Festuca arundinaceae* (7 *Lolium*+21 *F. arundinaceae*) such as the F2, F3, or later generations, which are produced from seed harvested from the panicles in the same manner as the previous embodiment.

Interspecific hybridization of the *L. multiflorum* inducer lines to generate dihaploid homozygous *Festuca* may be practiced with any Fescue species, provided that the Fescue is used as the paternal parent. Without being limited thereto, preferred Fescue species include Meadow Fescue, *F. pratensis*, and particularly Tall Fescue, *F. arunclinaceae*.

The dihaploid homozygous *Festuca* and dihaploid homozygous *Lolium* plants produced from the interspecific hybridization using either of the above mentioned techniques are fertile, and are inbred lines. Therefore, the plants may be used in the production of true F1 hybrids with any dihaploid line obtained from a like Fescue or *Lolium* species. Preferably, for the generation of true F1 hybrids, the dihaploid homozygous *Festuca* should be crossed with a dihaploid line representing the same *Festuca* species of interest.

The following examples are intended only to further illustrate the invention and are not intended to limit the scope of the invention that is defined by the claims.

EXAMPLE 1

Dihaploid Tall Fescue plants were produced using the process of the invention and examined to confirm that they were hossozygous/inbred lines.

In brief, the *L. multiflorum* inducer line IL-1 was crossed as the maternal parent with Tall Fescue, *F. arundinaceae*, as the paternal parent (pollen source) grown in a greenhouse. F1 interspecific hybrid seed is collected and planted into individual pots, and the F1 plants were allowed to grow, mature, and flower. After the panicle or seed heads matured, the seed heads were collected, gently ground, and sown in fresh potting soil. F2 plants were allowed to grow and plants appearing as normal Fescue by their broad leaves were examined and confirmed to be dihaploid Tall Fescue, containing 42 Fescue chromosomes with no *Lolium* chromosomes. Four of the dihaploid Fescue plants were retained for further analysis.

The four retained dihaploid Fescue plants were each selfed, and the seed was collected, planted, and allowed to grow. The offspring derived from the selfing were analysed by PCR-EST-SSR using eight highly discriminatory Tall Fescue markers. All offspring from each selfing were confirmed to be identical to each other by molecular analysis and were phenotypically identical to each other and their F2 dihaploid Fescue parent.

The identical molecular marker patterns exhibited across the offspring; and, their identical pattern to their F2 dihaploid parent, indicate a genetic uniformity and genetic homozygosity of the lines, allowing for the usage of the descriptive term 'dihaploid' to the F2 parent and its selfing generated offspring. These data also indicate the ability of the dihapioids to breed true to type by sibbing or selfing (i.e., uniformity with no genetic segregation).

It is understood that the foregoing detailed description is given merely by way of illustration and that modifications and variations may be made therein without departing from the spirit and scope of the invention.

I claim:

1. A novel *Lolium multiflorum* diploid plant or parts thereof having ATCC deposit accession number PTA-10229, wherein said *Lolium multiflorum* diploid plant segregates for levels of pollen sterility, and wherein upon using said *Lolium multiflorum* diploid plant as the maternal parent in an interspecific hybridization with a *Festuca* species, being utilized as the paternal parent, confers to the resultant sterile F1 interspecific hybrids the ability to produce some seed via parthenogenesis that also possess a viable embryo, and wherein said seeds which possess a viable embryo may develop into F2 generation plants, at least some of which are dihaploid homozygous *Festuca* species comprising a karyotype exhibiting a balanced genome of *Festuca* chromosomes equivalent to the chromosome number of said *Festuca* paternal parent and no *Lolium* chromosomes.

2. The progeny and parts thereof of said novel *Lolium multiflorum* diploid plant and parts thereof of claim 1, wherein said progeny segregates for levels of pollen sterility, and wherein upon using said progeny as the maternal parent in an interspecific hybridization with a *Festuca* species, being utilized as the paternal parent, confers to the resultant sterile F1 interspecific hybrids the ability to produce some seed via parthenogenesis that also possess a viable embryo, and wherein said seeds which possess a viable embryo may develop into F2 generation plants, at least some of which are dihaploid homozygous *Festuca* species comprising a karyotype exhibiting a balanced genome of *Festuca* chromosomes equivalent to the chromosome number of said *Festuca* paternal parent and no *Lolium* chromosomes, wherein said progeny and parts thereof contain the extranuclear genes of said *Lolium multiflorum* of claim 1.

3. The seed of said *Lolium multiflorum* of claim 1.

4. An ovule of said *Lolium multiflorum* of claim 1.

5. A tissue culture of regenerable cells of said *Lolium multiflorum* of claim 1.

6. A novel *Lolium multiflorum* diploid plant or parts thereof having ATCC deposit accession number PTA-10315, wherein said *Lolium multiflorum* diploid plant segregates for levels of pollen sterility, and wherein upon using said *Lolium multiflorum* diploid plant as the maternal parent in an interspecific hybridization with a *Festuca* species, being utilized as the paternal parent, confers to the resultant sterile F1 interspecific hybrids the ability to produce some seed via parthenogenesis that also possess a viable embryo, and wherein said seeds which possess a viable embryo may develop into F2 generation plants, at least some of which are dihaploid homozygous *Festuca* species comprising a karyotype exhibiting a balanced genome of *Festuca* chromosomes equivalent to the chromosome number of said *Festuca* paternal parent and no *Lolium* chromosomes.

7. The progeny and parts thereof of said novel *Lolium multiflorum* diploid plant and parts thereof of claim 6, wherein said progeny segregates for levels of pollen sterility, and wherein upon using said progeny as the maternal parent in an interspecific hybridization with a *Festuca* species, being utilized as the paternal parent, confers to the resultant sterile F1 interspecific hybrids the ability to produce some seed via parthenogenesis that also possess a viable embryo, and wherein said seeds which possess a viable embryo may develop into F2 generation plants, at least some of which are dihaploid homozygous *Festuca* species comprising a karyotype exhibiting a balanced genome of *Festuca* chromosomes equivalent to the chromosome number of said *Festuca* paternal parent and no *Lolium* chromosomes, wherein said progeny and parts thereof contain the extranuclear genes of said *Lolium multiflorum* of claim 6.

8. The seed of said *Lolium multiflorum* of claim 6.

9. An ovule of said *Lolium multiflorum* of claim 6.

10. A tissue culture of regenerable cells of said *Lolium multiflorum* of claim 6.

11. The *Lolium multiflorum* diploid plant or parts thereof of claim 6, wherein said seed that possess a viable embryo develops into F2 generation plants, at least some of which are dihaploid homozygous *Festuca* species comprising a karyotype of 42 *Festuca* chromosomes when said *Festuca* species paternal parent is Tall Fescue, *Festuca arundinaceae.*

12. The *Lolium multiflorum* diploid progeny of claim 7 or parts thereof, wherein said seed that possess a viable embryo develops into F2 generation plants, at least some of which are dihaploid homozygous *Festuca* species comprising a karyotype of 42 *Festuca* chromosomes when said *Festuca* species paternal parent is Tall Fescue, *Festuca arundinaceae.*

13. Seed of said *Lolium multiflorum* progeny of claim 7.

14. An ovule of said *Lolium multiflorum* progeny of claim 7.

15. A tissue culture of regenerable cells of said *Lolium multiflorum* progeny of claim 7.

16. The *Lolium multiflorum* diploid plant or parts thereof of claim 1 wherein said seed that possess a viable embryo develops into F2 generation plants at least some of which are dihaploid homozygous *Festuca* species comprising a karyotype of 42 *Festuca* chromosomes when said *Festuca* species paternal parent is Tall Fescue, *Festuca arundinaceae.*

17. The *Lolium multiflorum* diploid progeny of claim 2 or parts thereof wherein said seed that possess a viable embryo develops into F2 generation plants at least some of which are dihaploid homozygous *Festuca* species comprising a karyotype of 42 *Festuca* chromosomes when said *Festuca* species paternal parent is Tall Fescue, *Festuca arundinaceae.*

18. Seed of said *Lolium multiflorum* progeny of claim 2.

19. An ovule of said *Lolium multiflorum* progeny of claim 2.

20. A tissue culture of regenerable cells of said *Lolium multiflorum* progeny of claim 2.

\* \* \* \* \*